(12) United States Patent
Kang et al.

(10) Patent No.: US 9,222,946 B2
(45) Date of Patent: Dec. 29, 2015

(54) COMPOSITION OF DIAGNOSTIC BIOMARKER FOR STOMACH CANCER AND METHOD OF DIAGNOSING STOMACH CANCER USING THE COMPOSITION

(71) Applicant: KOREA INSTITUTE OF SCIENCE AND TECHNOLOGY, Seoul (KR)

(72) Inventors: Min-Jung Kang, Seoul (KR); Hafeza Akter, Seoul (KR); Oh-Seung Kwon, Seoul (KR); Won-Sang Park, Seoul (KR); Byung Hwa Jung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 250 days.

(21) Appl. No.: 13/792,542

(22) Filed: Mar. 11, 2013

(65) Prior Publication Data

US 2013/0323760 A1    Dec. 5, 2013

(30) Foreign Application Priority Data

May 29, 2012    (KR) .................. 10-2012-0056977

(51) Int. Cl.
*G01N 33/574*    (2006.01)
*G01N 33/68*    (2006.01)

(52) U.S. Cl.
CPC ...... *G01N 33/6893* (2013.01); *G01N 33/57446* (2013.01)

(58) Field of Classification Search
CPC  G01N 33/74; G01N 33/574; G01N 33/57446
USPC ............... 530/300, 327, 328, 387.1, 388.24; 435/7.1, 7.23; 436/64, 501
See application file for complete search history.

(56) References Cited

U.S. PATENT DOCUMENTS

2008/0280306 A1    11/2008  Ernst
2011/0166166 A1    7/2011   Henkin

FOREIGN PATENT DOCUMENTS

EP    1 424 557 A1    6/2004
JP    8-143597         6/1996

OTHER PUBLICATIONS

Tsalis et al. (Scand. J. Gastroenterol. Jun. 1990; 25 (6): 563-71).*
Probst-Cousin et al. (Clin. Neuropathol. Jan.-Feb. 2011; 30 (1): 18-24).*
Eriksson et al. (Acta Oncol. 1989; 28 (3): 373-7).*
Vasiadi et al. (Br. J. Dermatol. Sep. 2013; 169 (3): 695-9).*
Schimpff et al. (J. Neurol. Neurosurg. Psychiatry. Jun. 2011; 70 (6): 784-6).*
Miskowiak et al. (Regul. Pept. Nov. 1984; 9 (4): 263-9).*
Vadiadi et al. (Br. J. Dermatol. Jun. 2012; 166 (6): 1349-52).*
Sgourakis et al. (Tumour Biol. Jun. 2014; 35 (6): 5993-6002).*
Schimpff et al. (J. Neurol. Neurosurg. Psychiatry. Jun. 2001; 70 (6): 784-6).*
Davis et al. (J. Neurosci. Methods. Jun. 1985; 14 (1): 15-23).*
Korean Office Action dated Oct. 1, 2013 in corresponding Korean Office Application No. 10-2012-0056977.
"Promotion by Neurotensin of Gastric Carcinogenesis Induced by NMethyl-*N'*-nitro-*N*-nitrosoguanidine in Wistar Rats", Masaharu Tatsuta et al., Cancer Research, 1989, vol. 49, pp. 843-846.
Korean Notice of Allowance mailed Aug. 11, 2014, in corresponding Korean Patent Application No. 10-2012-0056977.
Leonard G. Davis et al., "The application of enzyme-linked immunosorbent assays (ELISA) to neuropeptides", Journal of Neuroscience Methods, vol. 14, 1985, pp. 15-23.
R-M Schimpff et al. "Increased plasma neurotensin concentrations in patients with Parkinson's disease", J Neurol Neurosurg Psychiatry, vol. 70, 2001, pp. 784-786.
Jean Claude Reubi et al., "Procholecystokinin as Marker of Human Ewing Sarcomas", Clinical Cancer Research, vol. 10, Aug. 15, 2004, pp. 5523-5530.
K. Zwirska-Korczala et al., "Basal and Postprandial Plasma Levels of Pyy, Ghrelin, Cholecystokinin, Gasrin and Insulin in Women With Moderate and Morbid Obesity and Metabolic Syndrome", J Physiology and Pharmacology, vol. 58, 2007, 17 pages.
Hafeza Akter et al., "Development of Cholecystokinin and Neurotensin as biomerkers in clinical samples using ELISA", Korean Society for Biochemistry and Molecular Biology, 2012 KSBMB Annual Meeting Abstract Submission, May 31, 2012, 3pages.

* cited by examiner

*Primary Examiner* — Stephen Rawlings
(74) *Attorney, Agent, or Firm* — Goldilocks Zone IP Law

(57) ABSTRACT

Provided are a composition of a diagnostic biomarker for stomach cancer and a method of diagnosing stomach cancer using the same. The composition of a diagnostic biomarker for stomach cancer and the method of diagnosing stomach cancer using the same may be useful to determine stomach cancer from a patient with suspected stomach cancer.

15 Claims, 4 Drawing Sheets

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapiens
<220> FEATURE:
<221> NAME/KEY: VARIANT
<222> LOCATION: (1)
<223> OTHER INFORMATION: pyrrolidone carboxylic acid
<220> FEATURE:
<221> NAME/KEY: VARIANT
<222> LOCATION: (13)
<223> OTHER INFORMATION: hydroxylation

<400> SEQUENCE: 1

Glu Leu Tyr Glu Asn Lys Pro Arg Arg Pro Tyr Ile Leu
  1               5                  10

<210> SEQ ID NO 2
<211> LENGTH: 8
<212> TYPE: PRT
<213> ORGANISM: Homo sapiens
<220> FEATURE:
<221> NAME/KEY: VARIANT
<222> LOCATION: (2)
<223> OTHER INFORMATION: sulfatation
<220> FEATURE:
<221> NAME/KEY: VARIANT
<222> LOCATION: (8)
<223> OTHER INFORMATION: amidation

<400> SEQUENCE: 2

Asp Tyr Met Gly Trp Met Asp Phe
  1               5
```

COMPOSITION OF DIAGNOSTIC BIOMARKER FOR STOMACH CANCER AND METHOD OF DIAGNOSING STOMACH CANCER USING THE COMPOSITION

CROSS-REFERENCE TO RELATED PATENT APPLICATION

This application claims the benefit of Korean Patent Application No. 10-2012-0056977, filed on May 29, 2012, in the Korean Intellectual Property Office, the disclosure of which is incorporated herein in its entirety by reference.

BACKGROUND OF THE INVENTION

1. Field of the Invention

The present invention relates to a composition of a diagnostic biomarker for stomach cancer and a method of diagnosing stomach cancer using the composition.

2. Description of the Related Art

Stomach cancer, which is one of the most prevalent diseases in South Korea and Japan, is the second most common disease to Koreans. Examples of risk factors of stomach cancer are family history, *Helicobacter pylori* infection, smoking, salty food, processed proteins, spoiled food, or the like, and they are mainly diagnosed through a gastrointestinal series. Regular gastroscopy may be performed to determine the seriousness of stomach cancer, but early detection thereof is difficult. Therefore, by discovering diagnostic markers that are clinically highly specific and sensitive and by using monoclonal antibodies to detect the diagnostic markers, a development of a kit that predicts early diagnosis of stomach cancer and progression of the disease may be promoted.

When measuring peptide markers in blood, there are interfering signals caused by several types of proteins (albumin, immunoglobulin, etc) that are present abundantly within the blood; therefore, when extracting the peptide markers from the blood, a molecular cut-off filter is used to increase a recovery rate.

In general, neurotensin and cholecystokinin are peptides involved in digestion; however, they are also involved in appetite control operating in the brain so that many studies focusing mainly on the operation and function of the brain are in progress so far. After the results of neuropeptide from a mouse brain tissue measured by an enzyme-linked immunosorbent assay (ELISA) were reported, it was then reported that the concentration of neurotensin in a blood sample from a patient with Parkinson's disease increased. Procholecystokinin was proposed as a diagnostic marker of a patient with human Ewing sarcoma. In addition, it was reported that neurotensin and cholecystokinin have been detected with high concentration to obese women in particular. However, with regard to stomach cancer, there is no report yet that neurotensin and cholecystokinin have been utilized as biomarkers.

Based on these reports, the inventors of the present invention measured the concentration of neurotensin and cholecystokinin, respectively, in a blood sample of a patient with stomach cancer and compared and analyzed the measurement with a blood sample of a normal patient. Thus, the inventors established neurotensin and cholecystokinin as diagnostic biomarkers for stomach cancer and also a method of diagnosing stomach cancer using the biomarkers.

SUMMARY OF THE INVENTION

The present invention provides a composition of a diagnostic biomarker for stomach cancer, a diagnostic kit including antibodies for the biomarker, and a method of diagnosing stomach cancer using the composition.

BRIEF DESCRIPTION OF THE DRAWINGS

The above and other features and advantages of the present invention will become more apparent by describing in detail exemplary embodiments thereof with reference to the attached drawings in which:

FIG. 3A refers to cholecystokinin while FIG. 3B refers to neurotensin; and, FIG. 4 is a graph comparing correlation between the concentration of neurotensin (in circle) and the concentration of cholecystokinin (in square) depending on the patients, and an x-axis refers to the patients while a y-axis refers to plasma concentration.

DETAILED DESCRIPTION OF THE INVENTION

Figure 1:
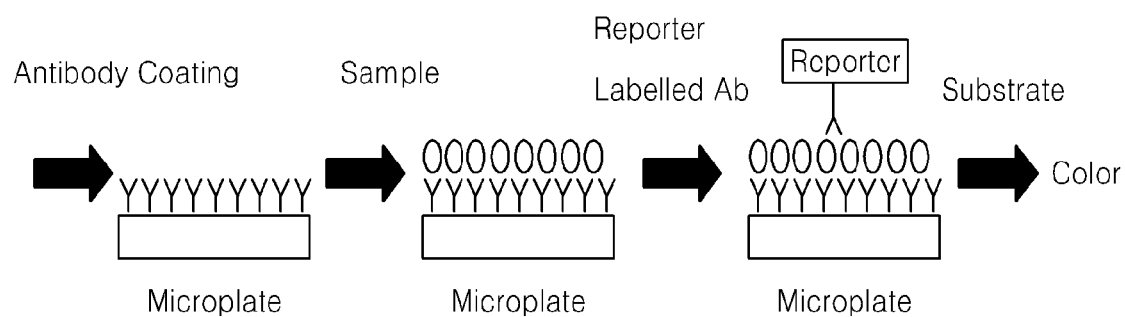
FIG. 1 is a view schematically illustrating an enzyme-linked immunosorbent assay (ELISA) by using monoclonal antibodies that are specific to neurotensin and cholecystokinin.

According to an aspect of the present invention, there is provided a composition of a diagnostic biomarker for stomach cancer that includes neurotensin having an amino acid sequence of SEQ ID. NO: 1, which increases the concentration in body fluids of a patient with stomach cancer compared to a normal person.

According to another aspect of the present invention, there is provided a composition of a diagnostic biomarker for stomach cancer that includes cholecystokinin having an amino acid sequence of SEQ ID. NO: 2, which reduces the concentration in body fluids of the patient with stomach cancer compared to the normal person.

According to an embodiment of the present invention, the body fluids may be selected from the group consisting of gastric juice, saliva, and blood, and most preferably, the body fluid is blood.

According to another aspect of the present invention, there is provided an antibody that is specific to neurotensin having an amino acid sequence of SEQ ID. NO: 1 or to a fragment thereof; and an antibody that is specific to cholecystokinin having an amino acid sequence of SEQ ID. NO: 2 or to a fragment thereof.

The fragment of the protein is, for example, an immunogenic fragment of biomarker proteins including at least one epitope that is able to be recognizable by antibodies for the biomarker proteins. According to another embodiment of the present invention, the antibodies for the biomarker proteins may be polyclonal antibodies or monoclonal antibodies, but monoclonal antibodies are preferred the most.

The polyclonal antibodies may be prepared by injecting the biomarker proteins or a fragment thereof as an immunogen into an external host, according to a method known to those of ordinary skill in the art. The external host may be mammal such as a mouse, a rat, a lamb, or a rabbit. When the immunogen is injected via intramuscular, intraperitoneal, or subcutaneous injection, adjuvant which is used to increase antigenicity is generally administered together. Then, by collecting blood from the external host on a regular basis, enhanced potency and antigen-specific serum may be collected or antibodies may be separated and purified therefrom.

The monoclonal antibodies may be prepared by cell line generation technology which is immortalized by fusion, which is known to one of ordinary skill in the art. A brief description of manufacturing the monoclonal antibodies is as follows.

The proteins are purified and an appropriate amount thereof (about 10 µg) is immunized in a Balb/C mouse, or a polypeptide fragment of the proteins is synthesized and immunized in a mouse along with bovine serum albumin. Thus, antigen-producing lymphocytes that are separated from the mouse are fused with human or mouse myeloma and produce a hybridoma. Then, cells of the hybridoma producing desired monoclonal antibodies were only selected and proliferated by using an enzyme-linked immunosorbent assay (ELISA), and thus, the monoclonal antibodies may be separated and purified from the culture.

A diagnostic kit for stomach cancer according to another embodiment of the present invention may be manufactured by a method which is known to one of ordinary skill in the art, and the kit typically includes antibodies and buffers in a freeze-dried form, stabilizers, inert proteins, or the like. The antibodies may be labeled by radionuclides, fluorophores, enzymes, or the like.

The monoclonal antibodies according to another embodiment of the present invention may be used not only in an immunoassay kit in various ways (e.g., ELISA, antibody-coated tube test, lateral-flow test, potable biosensor, etc), but also in a development of protein chips with a variety of stomach cancer detection spectrum based on the development of antibodies that are more highly specific and sensitive than any other antibodies.

For example, the kit may be used in an immunoassay, and a detection method of neurotensin and/or cholecystokinin is described based on the immunoassay. The immunoassay may be performed by a variety of immunoassay protocols or immunostaining protocols. Examples of the immunoassay or immunostaining formats are a radioactive immunoassay, a radioactive immunoprecipitation, an immunoprecipitation, an ELISA, a capture-ELISA, an inhibition or competitive analysis, a sandwich analysis, a flow cytometry, an immunofluorescent staining and immunoaffinity purification, but are not limited thereto. For example, when the present invention is performed by radioactive immunoassay, antibodies labeled with radioactive isotopes (e.g., $C^{14}$, $I^{125}$, $P^{32}$, and $S^{35}$) may be used to detect neurotensin and/or cholecystokinin.

When the kit is provided for an ELISA, a particular embodiment of the present invention using the kit may include methods of (i) coating primary antibodies specific to the fragment of neurotensin or cholecystokinin on a surface of a solid substrate; (ii) inducing an antigen-antibody reaction by contacting the primary antibody with blood samples of normal individual or individual with stomach cancer suspected (iii) reacting the resultants of the method (ii) with secondary antibodies that are coupled with enzymes; and (iv) detecting activity of the enzymes.

Appropriate examples of the solid substrate are hydrocarbon polymer (e.g., polystyrene and polypropylene), glass, metal or gel, and most preferable, a microtiter plate. The enzymes coupled with the secondary antibodies may include enzymes that catalyze a chromogenic reaction, a fluorescent reaction, a luminescent reaction, or an infrared reaction, but are not limited thereto. For example, examples of the enzymes are alkaline phosphatase, β-galactosidase, horseradish peroxidase, luciferase, and cytochrome $P_{450}$. When the alkaline phosphatase is used as the secondary antibody-binding enzyme, a substrate such as bromo-chloro-indolyl phosphate (BCIP), nitroblue terazolium (NBT), naphthol-AS-B1-phosphate and enhanced chemifluorescence (ECF), or chromogenic substrate may be used. When the horseradish peroxidase is used as the secondary antibody-binding enzyme, a substrate such as chloro-naphthol, amino ethyl carbazole, diamino benzidine, D-luciferin, lucigenin (bis-N-methylacridium nitrate), resorufin, luminal, M. Flex red reagent (10-acetyl-3,7-dihydroxxy phenoxazine), p-phenylenediamine-HCl and pyrocatechol (HYR), tetramethylbenzidine (TMB), 2,2'-Azine-di[3-ethylbenzthiazoline sulfonate] (ABTS), o-phenylene diamine (OPD) and naphthol/pyronin, and glucose oxidase and nitroblue tetrazolium (t-NBT) and phenzaine methosulfate (m-PMS) may be used.

According to another aspect of the present invention, there is a method of diagnosing stomach cancer including methods of detecting whether the concentration of neurotensin in the body fluids of the patient with suspected stomach cancer is relatively more increased than the normal person or whether the concentration of cholecystokinin is relatively more decreased than the normal person; and determining whether the patient with suspected stomach cancer has actual stomach cancer based on the detection results.

Examples of the body fluids include gastric juice, saliva, and blood, but are not limited there. Most preferably, the body fluid is blood.

The detecting in the method of diagnosing stomach cancer may be performed by measuring the concentrations of neurotensin and/or cholecystokinin based on the ELISA (coated tube) from the body fluids of the patient with suspected stomach cancer, a method using antibody-coupled magnetic particles or antibody-coupled latex particles, or the like.

One or more embodiments of the present invention will now be described in detail with reference to the following examples. However, these examples are not intended to limit the scope of the one or more embodiments of the present invention.

1. Protocol (1) Sample Preparation 500 ul of the blood samples from a normal person and a patient with stomach cancer, respectively, that are prepared by the School of Medicine, the Catholic University of Korea, were diluted twice with 10% formic acid buffer, and then peptides were extracted therefrom by using Oasis® HLB 1 cc (30 mg) Extraction Cartridges Solid phase Extraction Kit (Waters, Ireland). Serum and endogeneous peptides in serum and plasma were separated from the proteins and extracted by using a 10 kDa molecular cut-off filter (Millipore, USA). A solution containing the extracted peptide was dried by using $N_2$ Evaporator, Freeze-Dryer. For the immunological analysis, the solution was dissolved in 50 ul of assay buffer (Phoenix Pharmaceuticals Inc., USA), or 25 ul of the serum and the plasma was diluted twice with PBS buffer for the direct analysis. For LC-MS/MS analysis, the solution was dissolved in 100 ul of 0.2% formic acid in 50% methanol.

(2) ELISA

First, antibodies of neurotensin and cholecystokinin (primary antibodies, Phoenix Pharmaceuticals Inc., USA) present with a concentration in a range from about 0.2 to about 0.5 µg/Ml were coated on a microplate (SPL, Korea). Hereafter, the antibodies were reacted for 1 hour at room temperature by using PBS containing bovine serum albumin (BSA) in a concentration of 1 mg/Ml, and then prevented nonspecific reactions. Then, the prepared peptide solution or the diluted blood was reacted with the microplate. Then, the microplate was washed out with PCS containing 1% of Tween-20 to remove antigens that were not bound to the antibodies, and secondary antibodies were diluted at a ratio of 1:3,000 with PBS containing 1% of the BSA and reacted for 2 hours at room temperature. On the microplate, 100 μl of goat anti-human-IgG-HRP (Pierce) that was diluted at a ratio of 1:5,000 with PBS containing 1% of the BSA was added and reacted for 1 hour at room temperature, and then washed out with 1% PBS containing Tween-20. Lastly, in each well of the microplate, 100 μl of trimethylbenzidine (TMB) substrate (Sigma) was added to induce a chromogenic reaction, and then 50 μl of 2 N of $H_2SO_4$ solution was added to stop the reaction. Then, $OD_{450}$ values were measured by a microplate reader (Bio-Rad). Herein, standards in known concentrations (0.01, 0.1, 1, 10, 100 ng/ml, respectively) were measured as well to draw a calibration curve and calculate a concentration thereof. FIG. 1 is a view schematically illustrating methods of ELISA described above.

(3) Methods of Calculating Concentrations of Neurotensin and Cholecystokinin, Respectively The blood sample of a normal person or a patient with stomach cancer and an antigen standard (neurotensin or cholecystokinin) labeled with fluorescein isothiocyanate (FITC) were competitively reacted with magnetic beads that are coated with antibodies (Phoenix Pharmaceuticals Inc., USA). Then, the peptides and antigen standard that are precipitated without binding within the blood were washed out with PBS containing 1% Tween-20 and analyzed by using flow cytometry (Beckmann Coulter Inc., USA) to calculate concentrations of neurotensin and cholecystokinin, respectively. In the case of using the flow cytometry, an accurate calculation based on the calibration curve is difficult to do so that the calculation was done by using a method to determine a positive and a negative with reference to the results of analysis by the standards (concentration of cut-off value).

On the other hand, the concentrated extract blood from the prepared peptides was analyzed with peptide standards in known concentrations (0.01, 0.1, 1, 10 100 ng/ml, respectively) by using multi reaction monitoring (MRM) of LC-MS/MS (LTQ-Orbitrap, Thermo Scientific), and then a calibration curve is drawn to the area of the chromatogram obtained from the standard solution. Based on this, the concentration of neurotensin and cholecystokinin in the blood was measured. Conditions of the LC that was used were as follows:

Mobile Phase:
A 10% Acetonitrile in $dH_2O$ with 0.2% formic acid
B 10% $dH_2O$ in Acetonitrile with 0.2% formic acid
Flow rate: 0.2 mL/min
Gradient: B 0%→0% (2 min), 0%→20% (23 min), 20%→35% (5 min), 35%→40% (8 min), 40%→70% (10 min), 70%→100% (5 min, hold 5 min), 100%→100% (2 min)

On the other hand, conditions of the MRM that was used to detect the peptides were shown in Table 1.

TABLE 1

| Compound | Parent ion | Monitoring fragment ion |
|---|---|---|
| Neurotensin | 837.9 | 780.6 |
| CCK | 1064.0 | 1047.0 |

2. Experimental Results

Figure 2:
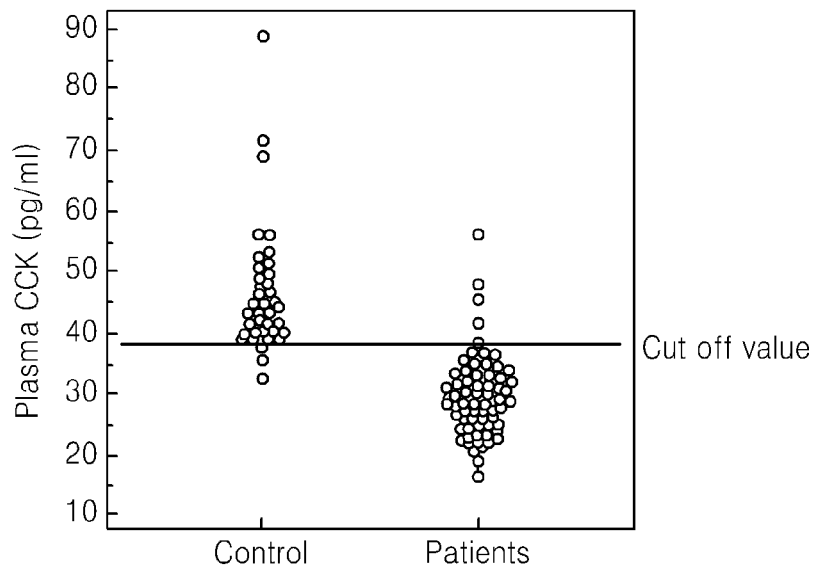
FIGS. 2A and 2B are graphical views illustrating results of analyzing concentrations of neurotensin (NT) and cholecystokinin (CCK) in blood samples from a normal person and a patient with stomach cancer, respectively. In the case of a patient with stomach cancer, the concentration of NT is significantly high ($p<0.005$) or the concentration of CCK is low compared to the normal person. In addition, cut-off values are set at 38 pg/ml (CCK) and 237 pg/ml (NT) (confidence interval 95%), respectively.
Figure 2:
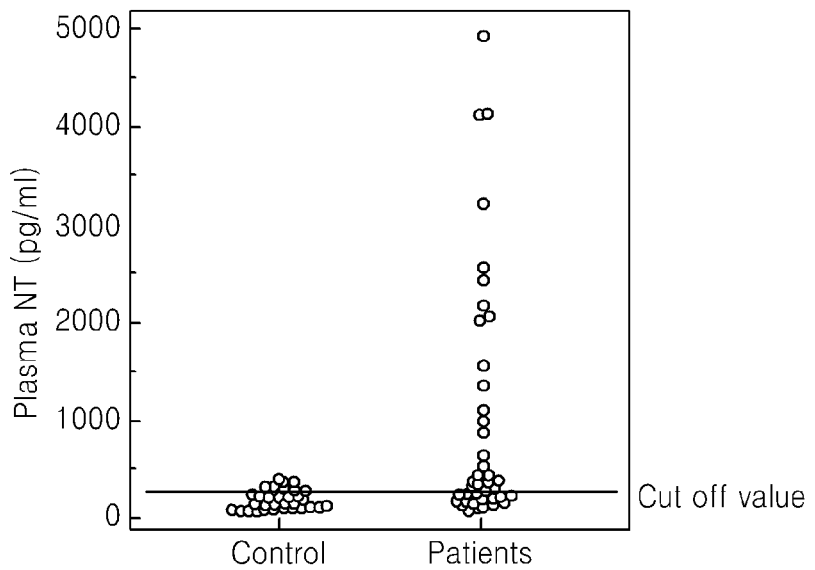

As a result of ELISA analyzing concentrations of neurotensin and cholecystokinin from the samples from a normal person and a patient with stomach cancer, respectively, as shown in FIG. 2, a significantly high concentration of neurotensin was detected from the sample of the patient with stomach cancer compared to that of the normal person. Also, a significantly low concentration of cholecystokinin was detected from the sample of the patient with stomach cancer compared to that of the normal person.

Figure 3:
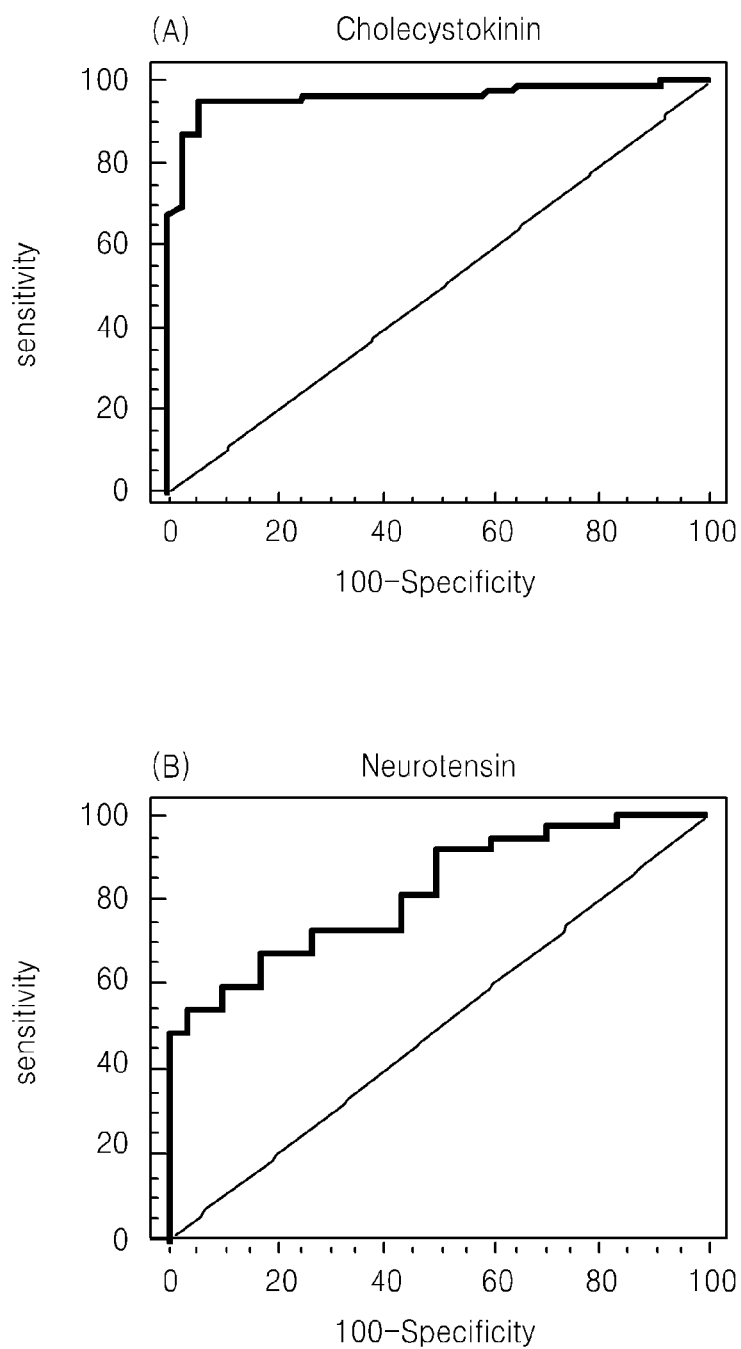
FIGS. 3A and 3B are graphical views illustrating curves of receiver operating characteristic (ROC) for a normal person and a patient with stomach cancer, respectively.

As shown in FIG. 3, in addition, the ROC curve that was drawn based on the measured concentrations of neurotensin and cholecystokinin from the blood samples of a patient with stomach cancer and a normal person, the neurotensin showed 83% of the specificity and 72% of the sensitivity, respectively. Herein, a criterion was 237 pg/ml. In the case of cholecystokinin, the ROC curves showed 94% of the specificity and 95% of the sensitivity and a criterion was 38 pg/ml. Each area under curve (AUC) in the ROC curve was 0.95 in cholecystokinin and 0.81 in neurotensin (see Table 2). As a result, the two markers were specific to disease and were found out to be very useful as diagnostic markers for stomach cancer.

TABLE 2

| Parameters | CCK | NT |
|---|---|---|
| Cutoff value (pg/ml) | 38 | 237 |
| AUC | $0.95 \pm 0.018^{a,b}$ | $0.81 \pm 0.05^{a,b}$ |
| Specificity | 94.4% | 83.3% |
| Sensitivity (95% CI) | 94.7% (86-98) | 71.6% (53-85) |

AUC, area under the curve; CI, confidence interval;

[a]AUC ± standard error

[b]All p < 0.0001 when comparing AUC for CCK and NT

Sensitivity and specificity of each assay were calculated using a cutoff value of CCK, NT, respectively.

Figure 4:
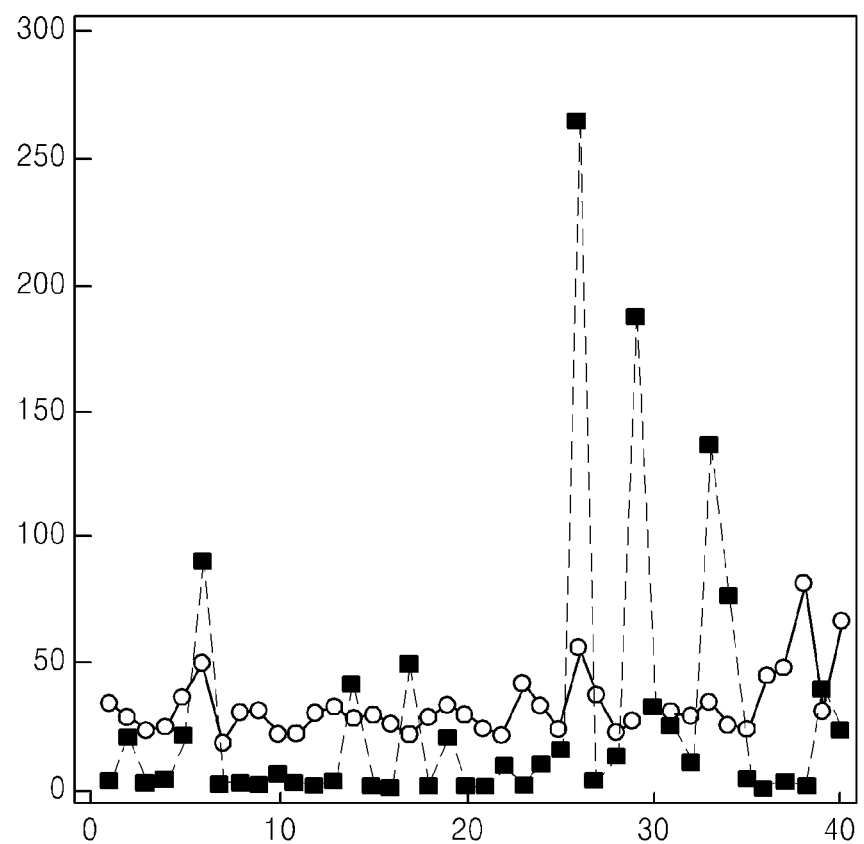

As shown in FIG. 4, in addition, the results of the correlation between concentration of neurotensin and that of cholecystokinin compared by each patient showed that concentration of neurotensin and that of cholecystokinin were generally inversely proportional to each other. As a result, if the two markers of neurotensin and cholecystokinin were simultaneously used in the diagnosis, a more accurate diagnosis would have been conducted.

According to another embodiment of the present invention, the composition of a diagnostic biomarker for stomach cancer and the method of diagnosing stomach cancer using the composition may be useful to determine whether a patient with suspected stomach cancer has stomach cancer or not.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of diagnosing stomach cancer comprising:
   measuring the concentrations of neurotensin and cholecystokinin in the blood of a patient with suspected stomach cancer;
   determining if the concentration of neurotensin in the blood of the patient is greater than 237 pg/ml and if the concentration of cholecystokinin in the blood of the patient is less than 38 pg/ml; and
   determining that the patient has stomach cancer when the concentration of neurotensin in the blood of the patient is greater than 237 pg/ml and the concentration of cholecystokinin in the blood of the patient is less than 38 pg/ml,
   or determining that the patient does not have stomach cancer when the concentration of neurotensin in the blood of the patient is not greater than 237 pg/ml or when the concentration of cholecystokinin in the blood of the patient is not less than 38 pg/ml.

2. The method of claim 1, wherein neurotensin has the amino acid sequence of SEQ ID. NO: 1.

3. The method of claim 1, wherein cholecystokinin has the amino acid sequence of SEQ ID. NO: 2.

4. The method of claim 1, wherein the concentration of neurotensin is measured using an antibody specifically binding to neurotensin having the amino acid sequence of SEQ ID. NO: 1 or to a fragment thereof.

5. The method of claim 1, wherein the concentration of cholecystokinin is measured using an antibody specifically binding to cholecystokinin having the amino acid sequence of SEQ ID. NO: 2 or to a fragment thereof.

6. The method of claim 1, wherein the concentration of neurotensin or the concentration of cholecystokinin is measured by immunoassay or immunostaining.

7. The method of claim 1, wherein the concentration of neurotensin or the concentration of cholecystokinin is measured by assay selected from the group consisting of radioactive immunoassay, radioactive immunoprecipitation, immunoprecipitation, enzyme-linked immunosorbent assay (ELISA), flow cytometry, immunofluorescent staining, and immunoaffinity purification.

8. A method of diagnosing stomach cancer comprising:
   measuring the concentrations of neurotensin and cholecystokinin in the blood of a patient with suspected stomach cancer;
   determining if the concentration of neurotensin in the blood of the patient is greater than 237 pg/ml and if the concentration of cholecystokinin in the blood of the patient is less than 38 pg/ml; and
   determining that the patient has stomach cancer when the concentration of neurotensin in the blood of the patient is greater than 237 pg/ml and the concentration of cholecystokinin in the blood of the patient is less than 38 pg/ml,
   or determining that the patient does not have stomach cancer when the concentration of neurotensin in the blood of the patient is not greater than 237 pg/ml or when the concentration of cholecystokinin in the blood of the patient is not less than 38 pg/ml,
   wherein neurotensin has the amino acid sequence of SEQ ID. NO: 1, and wherein cholecystokinin has the amino acid sequence of SEQ ID. NO: 2.

9. The method of claim 8, wherein the concentration of neurotensin or the concentration of cholecystokinin is measured by immunoassay or immunostaining.

10. The method of claim 8, wherein the concentration of neurotensin or the concentration of cholecystokinin is measured by assay selected from the group consisting of radioactive immunoassay, radioactive immunoprecipitation, immunoprecipitation, enzyme-linked immunosorbent assay (ELISA), flow cytometry, immunofluorescent staining, and immunoaffinity purification.

11. The method of claim 10, wherein the assay is ELISA.

12. A method of diagnosing stomach cancer comprising:
    measuring the concentrations of neurotensin and cholecystokinin in the blood of a patient with suspected stomach cancer;
    determining if the concentration of neurotensin in the blood of the patient is greater than 237 pg/ml and if the concentration of cholecystokinin in the blood of the patient is less than 38 pg/ml; and
    determining that the patient has stomach cancer when the concentration of neurotensin in the blood of the patient is greater than 237 pg/ml and the concentration of cholecystokinin in the blood of the patient is less than 38 pg/ml,
    or determining that the patient does not have stomach cancer when the concentration of neurotensin in the blood of the patient is not greater than 237 pg/ml or when the concentration of cholecystokinin in the blood of the patient is not less than 38 pg/ml,
    wherein the concentration of neurotensin in measured using an antibody specifically binding to neurotensin having the amino acid sequence of SEQ ID. NO: 1 or to a fragment thereof, and
    the concentration of cholecystokinin in measured using an antibody specifically binding to cholecystokinin having the amino acid sequence of SEQ ID. NO: 2 or to a fragment thereof.

13. The method of claim 12, wherein the concentration of neurotensin or the concentration of cholecystokinin is measured by immunoassay or immunostaining.

14. The method of claim 12, wherein the concentration of neurotensin or the concentration of cholecystokinin is measured by assay selected from the group consisting of radioactive immunoassay, radioactive immunoprecipitation, immunoprecipitation, enzyme-linked immunosorbent assay (ELISA), flow cytometry, immunofluorescent staining, and immunoaffinity purification.

15. The method of claim 14, wherein the assay is ELISA.

* * * * *